United States Patent
Kross et al.

(10) Patent No.: US 9,393,184 B2
(45) Date of Patent: Jul. 19, 2016

(54) OXYCHLORINE ORAL RINSE COMPOSITION HAVING ENHANCED ORAL-TISSUE COMPATIBILITY FOR THE DESTRUCTION OF MALODORANTS, THEIR PUTREFACTIVE MICROBIAL SOURCES AND GUM-DISEASE PATHOGENS AND A METHOD FOR THE PREPARATION THEREOF

(71) Applicants: Robert D. Kross, Bellmore, NY (US); Nicholas D. Mulder, Philadelphia, NY (US)

(72) Inventors: Robert D. Kross, Bellmore, NY (US); Nicholas D. Mulder, Philadelphia, NY (US)

(73) Assignee: ProFresh Properties Inc., Philadelphia, PA (US)

( * ) Notice: Subject to any disclaimer, the term of this patent is extended or adjusted under 35 U.S.C. 154(b) by 237 days.

(21) Appl. No.: 14/182,754

(22) Filed: Feb. 18, 2014

(65) Prior Publication Data

US 2014/0341819 A1    Nov. 20, 2014

Related U.S. Application Data

(60) Provisional application No. 61/855,509, filed on May 17, 2013.

(51) Int. Cl.
*A61K 8/20* (2006.01)
*A61Q 11/00* (2006.01)
*A61Q 17/00* (2006.01)

(52) U.S. Cl.
CPC . *A61K 8/20* (2013.01); *A61Q 11/00* (2013.01); *A61Q 17/005* (2013.01)

(58) Field of Classification Search
USPC .......................... 424/53, 65, 601, 661; 216/33
See application file for complete search history.

(56) References Cited

U.S. PATENT DOCUMENTS

| | | | |
|---|---|---|---|
| 3,271,242 A * | 9/1966 | McNicholas | A21D 2/02 424/53 |
| 4,574,084 A * | 3/1986 | Berger | A01N 59/00 424/601 |
| 5,380,518 A | 1/1995 | Roozdar | |
| 5,389,384 A * | 2/1995 | Jooste | A01N 59/00 424/661 |
| 5,738,840 A | 4/1998 | Richter | |
| 6,231,830 B1 | 5/2001 | Madray | |
| 7,429,556 B2 | 9/2008 | Delcomyn et al. | |
| 2009/0152237 A1 * | 6/2009 | Chiang | C04B 37/021 216/33 |
| 2010/0233101 A1 | 9/2010 | Grotveid et al. | |
| 2010/0330203 A1 | 12/2010 | Kross et al. | |
| 2011/0104081 A1 | 5/2011 | Scott et al. | |

FOREIGN PATENT DOCUMENTS

WO   WO 2010/0853323 A1   7/2010

OTHER PUBLICATIONS

Rautemaa et al., "Oral infectins and systemic disease—an emerging problem in medicine." Clin Microbial Infect 2007;13:1041-1047.*
PCT International Search Report (ISA/US) for Kross et al., P.C.T. Application No. PCT/US2014/031954 (Aug. 20, 2014).
PCT Written Opinion of the International Searching Authority (ISA/US) for Kross et al., P.C.T. Application No. PCT/US2014/031954 (Aug. 20, 2014).

* cited by examiner

*Primary Examiner* — Walter Webb
(74) *Attorney, Agent, or Firm* — Edwin D. Schindler

(57) ABSTRACT

An antimicrobial oxychlorine oral rinse composition for preventing and treating oral malodor and diseases, tooth decay with improved palatability and tissue compatibility, includes an aqueous chlorine dioxide and chlorite ion solution with the chlorite ion predominating in the multiple oxychlorine rinse composition. A method for preparing such antimicrobial oxychlorine oral rinse composition comprising 3 ppm to about 200 ppm of chlorine dioxide, by first preparing an aqueous solution with about 7 to 400 ppm of chlorite ion; then an aqueous acidifying agent concentrate which, upon introduction to the chlorite solution, reduces its pH to about 4.5 to 6.0; then a second aqueous buffer-producing oxidant combination concentrate. The first acidifying agent concentrate is added to the chlorite ion solution and the second aqueous buffer-producing oxidant combination concentrate is added to the acidified chlorite ion solution, producing an antimicrobial oxychlorine oral rinse composition at about 5.0 to 6.8 pH.

12 Claims, No Drawings

OXYCHLORINE ORAL RINSE COMPOSITION HAVING ENHANCED ORAL-TISSUE COMPATIBILITY FOR THE DESTRUCTION OF MALODORANTS, THEIR PUTREFACTIVE MICROBIAL SOURCES AND GUM-DISEASE PATHOGENS AND A METHOD FOR THE PREPARATION THEREOF

CROSS-REFERENCE TO RELATED APPLICATION

The inventors claims domestic priority, pursuant to 35 U.S.C. §119(e), on the basis of U.S. Provisional Patent Application No. 61/855,509, filed May 17, 2013, the entire disclosure of which shall be deemed to be incorporated by reference herein.

BACKGROUND OF THE INVENTION

1. Technical Field of the Invention

The present invention relates generally to oxychlorine oral rinse compositions that combine improved palatability and tissue compatibility with the dual ability to reduce oral malodor and eliminate microbial pathogens associated with gum diseases, and methods for the preparation of such compositions.

More particularly, the present invention relates to oxychlorine oral rinse compositions that are effective against oral malodorancy by oxidatively destroying both the chemical species that characterize oral malodorants and the putrefactive microorganisms that create it. The oxychlorine compositions of the present invention comprise both chlorine dioxide and chlorite ion in an optimum ratio for providing supplementary oxidative activity from the complex anion produced therefrom.

2. Description of the Prior Art

Malodor of the oral cavity, and all related terms such as "bad breath," "halitosis," "foul breath" and "breath malodor," generally refer to the offensive breath odor of one person as detected by another. It has been estimated that 90% of the population exhibit oral malodor upon arising (e.g., "morning mouth") which persists throughout the day in about 20% of American adults. Such oral malodor is often not directly detectable by the sufferer, who only becomes aware by the revealing actions of others. In addition to immediate embarrassment, oral malodor can cause a significant interference with the enjoyment of everyday life, affecting career advancement as well as family and societal relationships.

Contrary to popular belief, at least 90% of the malodors in healthy persons are produced by local oral conditions. Normal lung air and stomach aroma do not significantly contribute to oral malodor, although various localized respiratory infections, organ system diseases, medications and metabolic disorders can cause malodorous breath. The causes of "morning mouth" and the bad breath which lasts through the day are basically the same, i.e., the putrefactive activity of certain oral bacteria on the sulfur-containing amino acids in oral organic matter such as cellular debris, food particles and salivary proteins. This degradation by anaerobic bacteria results in the formation of volatile, odiferous sulfur compounds, consisting primarily of hydrogen sulfide, methyl mercaptan, and to a lesser extent other thiols and disulfides, which are then exhaled in the breath. The products are called by the group term "volatile sulfur compounds" (VSCs) and may be detectable in air at parts per billion levels. In sleep, depleted local oxygen availability, lower salivary flow, and the reduced action of the tongue and cheeks, enhance the action of these bacteria. These effects, however, are overcome by most healthy people in the waking state.

Mouthwash users seem to experience little lasting effect from such use, since these formulations generally act as temporary masking agents that briefly supplant the malodor with a more pleasant one. Such rinses may also wash away some of the organic debris upon which the bacteria thrive, but they cannot eliminate the root cause of the malodor in those who are prone to the condition.

The prior art includes treatments for halitosis whereby the oral cavity is rinsed with an aqueous solution of so-called "stabilized chlorine dioxide." Examples include U.S. Pat. Nos. 5,200,171; 4,837,009; 4,808,389; 4,793,989; 4,792,442; 4,788,053; 4,786,492; 4,696,811; 4,689,215; 4,851,213; all issued to Perry A. Ratcliff. These patents are all directed to compounds or methods for treating malodors of the mouth, which involve the inaptly termed "stabilized chlorine dioxide." The expression "stabilized chlorine dioxide" ("SCD") as used by Ratcliff in his patents, rather than being directed to molecular chlorine dioxide which has been stabilized in some fashion, actually refers to an aqueous solution whose active agent comprises sodium chlorite. Confusion arises because SCD is actually sodium chlorite in solution, which may be formed, for example, by reconverting any chlorine dioxide that is created in a degrading chlorite solution back to chlorite ion, using an oxidant such as hydrogen peroxide. The reaction results in the reduction of the chlorine dioxide to chlorite ion, which can remain in alkaline solutions for extended periods of time. Another method used to produce SCD is to add bulk sodium chlorite to water in combination with a buffer or a peroxy compound, which will stabilize the chlorite and prevent it from slowly converting to chlorine dioxide. In sum, a solution of SCD as described in the art need not contain any significant or even measurable quantities of molecular chlorine dioxide per se, and in reality such solutions are comprised of chlorite salts at alkaline pHs, generally ±pH 9-9.5 (cf. 2% and 5% SCD, as sold by DuPont). The tendency of sodium chlorite to slowly transform to chlorine dioxide, as well as to other inactive chlorine species, is the basis for the claimed activity of SCD solutions in correcting oral malodor. In the Ratcliff patents, for example, the SCD is reported to be present in concentrations which ostensibly produce between 0.05% and 0.1% chlorine dioxide, which corresponds to actual sodium chlorite levels of 0.067% and 0.134% in the solution. The "transformation" to chlorine dioxide is purportedly triggered by acidic microorganisms in the oral cavity, as further mentioned below.

A current, commercially-available composition (ProFresh®) offers effective control of oral mouth odor. Its active ingredient is soluble chlorine dioxide gas, in contrast to the chlorite-based, so-called "stabilized chlorine dioxide"; the basis for other compositions advertised for many years to treat mouth malodor. SCD, as a poor oxidant, is widely considered to be relatively ineffective in controlling oral malodors compared to the dissolved gaseous molecular chlorine dioxide present in the ProFresh® composition. The latter product contains molecular chlorine dioxide, i.e., $ClO_2$, at a level of ca. 40 parts per million (ppm). $ClO_2$ is a good oxidant, although $ClO_2$ solutions are not stable, unless stored under appropriate conditions, and are normally prepared on-site for water disinfection. The ProFresh® product, following $ClO_2$ production by the user, has a useful life of months, owing to its storage in minimally-diffusive polymer containers. Aqueous chlorite (also known as stabilized chlorine dioxide) solutions, which are substantially poorer oxidants, are relatively stable for extended periods at the near-normal pH values of SCD dilutions. SCD will purportedly transform gradually to free (active) $ClO_2$ in an oral environment at much too slow a rate to produce sufficient levels of $ClO_2$ to effectively destroy any significant levels of oral malodorants during the brief contact associated with mouth rinsing.

Oral Microbial Considerations:

These relate to the microorganisms that are responsible for the production of oral malodorants, those responsible for dental plaque and those associated with periodontal disease. With regard to their role in malodor, as mentioned above, the putrefactive activity of certain oral bacteria results in the formation of volatile, odiferous sulfur compounds, such as hydrogen sulfide, methyl mercaptan, and other thiols and disulfides, which are in people's breath. These microorganisms, which primarily reside within tongue surfaces, are anaerobes and facultative anaerobes, which thrive in low oxygen environments.

There is another group of microorganisms, those which are associated with biofilm formation. Dental plaque is a biofilm, and there are about 1,000 species of bacteria that are involved in the formation of dental biofilm. The microorganisms that form the biofilm are mainly the facultative *Streptococcus mutans* and the true anaerobes, for which examples of such anaerobes include *fusobacterium* and actinobacteria. Dental plaque forms on both the enamel of the teeth, the surface of the root or dental implants and are embedded in an exopolysaccharide matrix. The bacteria most frequently associated with periodontal disease in humans, whether biofilm formers or not, are as follows (all classified as Gram-negative pathogens): *Actinobacillus actinomycetemcomitans, Porphyromonas gingivalis, Prevotella intermedia, Bacteroides forsythus, Campylobacter rectus, Treponema* spp. and *Eubacterium* spp (which include both Gram-negative and Gram-positive organisms). While there are a number of antibiotics and antimicrobials (e.g., Doxycycline, chlorhexidine gluconate) which are effective in destroying many of these pathogens, those such as the biofilm-forming *Porphyromonas gingivalis* pose significant difficulty.

Kross, et al., in U.S. Pat. No. 6,599,432, taught a method for reducing or eliminating microbial flora associated with biofilms in small diameter dental water lines, in which levels of $ClO_2$ of about 500 ppm to about 2,500 ppm were highly effective in penetrating biofilms, and without being vitiated by reaction with the exo-polysaccharide structure of the biofilms, could destroy most, if not all, of the organisms residing therein after a contact time of at least about 30 minutes. This achievement has recently raised the speculation of whether a much smaller concentration of $ClO_2$, at ca. 40 ppm, which is one twelfth the 500 ppm concentration, and with a contact time of perhaps one sixtieth of typical rinse times maximum being generally about 30 seconds), would provide some ability to destroy microorganisms in oral biofilms.

With respect to the ability molecular $ClO_2$ systems to treat oral diseases, such as gingivitis and periodontitis, the literature and prior patent art is silent: Ratcliff in U.S. Pat. No. 4,696,811 teaches the use of SCD for the reduction of dental plaque and the inhibition of the growth of the microorganisms primarily responsible for plaque formation. But reducing plaque formation, if indeed the SCD (chlorite solutions) did show some efficacy in that regard, in no manner provides evidence that it can remediate oral diseases. The composition taught in U.S. Pat. No. 5,281,412 is claimed to provide anti-plaque and anti-gingivitis benefits. The composition comprises chlorite and citrate ion compositions at a pH from about 5.9 to about 6.5. While directed to the antimicrobial control of oral disease conditions, in the defined pH range, little if any $ClO_2$ could be liberated in a timely manner, in that pH range, by the disproportionation of chlorous acid to form it.

Oral Cavity Compatibility:

A number of factors are relevant with regard to the present invention, which incorporates significant discoveries in the use of molecular $ClO_2$ solutions for oral care treatment, for which $ClO_2$ has been well validated as the most effective treatment of oral malodor.

Concentration
Palatability Osmotic Pressure
Concentration:

The current ProFresh® oral rinse involves the "activation" of a dilute sodium chlorite solution in a two-step process of acidification followed by addition of hypochlorite to create a $ClO_2$ solution of ca. 40 ppm, where there is a large excess of residual chlorite ion. It has been shown by Kross in U.S. Pat. No. 6,284,152, that some excess of chlorite ions in such solutions is decidedly advantageous. The advantage reported in the foregoing patent is that the residual chlorite ion will allow for the continued production of $ClO_2$, after activation and storage of the solution, to compensate for evaporative losses by both periodic opening of the bottle by the consumer and diffusional losses through container walls. This continued slow generation comes about because, at the average pH of the activated solution (ca. 6±0.5), there will be a slow disproportionation of the low level of chlorous acid [$HClO_2$] present in equilibrium with the chlorite ion (from $NaClO_2$) in solution, to create additional $ClO_2$. In the marketed ProFresh® product, the present inventors have calculated that the ratio of chlorite ion to $ClO_2$ after its partial oxidation to ~40 ppm $ClO_2$ (~1120−40=1080 ppm chlorite) is ca. 27 [$ClO_2$:$ClO_2$]. In U.S. Pat. No. 6,284,152, Kross teaches that "the molar ratio of chlorite ion to $ClO_2$ in said solutions (should) range from about 20:1 to about 1:1, more preferably about 15:1 to about 1:1, most preferably about 10:1 to about 1:1." The ratio of 27:1 in the marketed product is therefore above the preferred range and significantly above the most preferred range of about 10:1 to about 1:1. There are several disadvantages attendant to the excess chlorite levels in these solutions which, though they provide continued product uniformity, have a definite negative physiological impact.

Concentration and Perceived and Objectionable "Saltiness" of the Oral Rinse:

With regard to the oral cavity, the compatibility of a chlorite-based oral rinse containing molecular $ClO_2$ as the basis for oral malodor control, these inventors have determined that the absolute and relative levels of chlorite salt, with respect to $ClO_2$ concentration, are substantially inferior to such a system where due consideration is given to that level with regard to taste and osmotic pressure. We have realized that a much reduced level of chlorite ion is required, with respect to the $ClO_2$ level, in order to satisfy both criteria.

Concentration and Incompatibility of the Oral Rinse with Normal Saliva Vis-á-Vis Osmotic Pressure:

With respect to osmotic pressure, this parameter is directly related to the soluble components comprising an aqueous system, as is saliva. A technical publication from Sawinski et al., almost half-a-century ago, reported that the mean osmotic pressure of human saliva is 38 millosmoles/liter (mosm/L), which is mid-range of the 21-77 mosm/L for the subjects in their study. For reference purposes, the osmotic pressure of human blood plasma (which perfuses human tissues) is ~165 mosm/L. It is desirable, therefore, to devise an oral rinse that would approximate and be optimally compatible with the osmotic pressure of that 21-77 range, and come close to the mean value of 38 in cellular tissue, if possible. The osmotic pressure of the current imbalanced ProFresh product, with a surfeit of chlorite salt, is calculated to be 165 mosm/L, after activation to yield ca., 40 ppm of $ClO_2$. This is approximately 4 times higher than the 38 mosm/L mean osmotic pressure in human saliva. What had to be determined is whether a dilution of the chlorite salt level in the current ProFresh® product, to comport with, or even approximate that lower value of saliva, would be consistent with the continued documented malodorizing functionality of that oral rinse, while concomitantly alleviating much or all of the negative perceived taste of the product.

Oral Pathogens and Biofilms

Oral microbial biofilms, which are implicated in plaque and periodontal disease, are found on such surfaces as the enamel of the teeth, the surface of the root or dental implants. Biofilms are three-dimensional structured bacterial communities attached to a solid surface submerged in, or exposed to some aqueous solution. Biofilms consist of many species of bacteria living within a matrix of excreted polysaccharides, which protect the cells within it. Bacteria living in a biofilm can have significantly different properties from free-floating bacteria, as the dense and protected environment of the film allows them to cooperate and interact in various ways. One benefit of this environment is increased resistance to substances dissolved in saliva, such as antibiotics, since the dense extra-cellular matrix and the outer layer of cells protect the interior of the community.

Dental plaque is a yellowish biofilm that builds up on the teeth. If not removed regularly, it can lead to dental caries. Caries, gingivitis and periodontitis are infectious diseases. One typical study showed that in subgingival plaque the most abundant species from different phyla and species associated with periodontitis were *Actinomyces* sp., *Tannerella forsythia*, *Fusobacterium nucleatum*, *Spirochaetes*, and *Synergistetes*. It also identified *Lactobacillus* spp. in subgingival plaque, and *Streptococcus* spp. and the yeast *Candida albicans* in supragingival plaque. These organisms are obviously different from the ones cited earlier that are associated with periodontal disease. What is common to both groups is the biofilm-forming *Strep. mutans* associated with dental plaque and *Porphyromonas gingivalis* associated with periodontal disease.

With respect to periodontal disease, it affects one or more of the periodontal tissues, i.e., alveolar bone, periodontal ligament, cementum and gingival. Plaque-induced inflammatory lesions make up the vast majority of periodontal diseases, which are divided into two categories, namely, gingivitis and periodontitis, where gingivitis always precedes periodontitis. Traditionally, the treatment of periodontal disease begins with the removal of subgingival calculus and biofilm deposits. The bacteria responsible for most periodontal disease are anaerobic, and oxygenation reduces, but doesn't eliminate populations. A typical treatment involves the mechanical delivery of hydrogen peroxide to subgingival pockets via a water pick. Another method involves the use of an orally administered antibiotic, Periostat (Doxycycline). While the antibiotic decreases alveolar bone loss and improves the conditions of periodontal disease, is does not kill the bacteria; it only inhibits the body's host response to destroy the tissue. The more recent laser-assisted periodontal therapy has been shown to kill the bacteria that cause periodontal disease, but requires appropriate equipment and dental expertise to practice. Thus, no treatments or even preventive measures exist in the art, providing efficient, rapid and inexpensive control and elimination of periodontal diseases in persons afflicted by, or subject to these conditions. One of the major foci of this invention is the remediation of this situation.

Potential Role of Chlorine Dioxide ($ClO_2$) and Oxychlorine Solutions in the Amelioration of Periodontal Disease Biofilm control, in such areas as the food industry and in water processing (including dental office water supplies), is often effected using strong oxidizing agents. Although chlorine dioxide ($ClO_2$) is being used increasingly to control microbiological growth in a number of different industries, not much is known about disinfection of biofilms with chlorine dioxide. The unique ability demonstrated by $ClO_2$ to destroy biofilm-encased organisms, as with say chlorine ($Cl_2$), usually used in water purification, is universally attributed to the differing oxidation capacities of both species. As per a citation in an article on $ClO_2$ by the Saber company, a purveyor of $ClO_2$ systems: "Chlorine is a more powerful oxidizer than chlorine dioxide, and will react with a wider variety of chemicals. This property limits its overall effectiveness as a biocide. Conversely, because chlorine dioxide has more oxidative capacity compared to ozone or chlorine, less chlorine dioxide is required to obtain an active residual concentration of the material when used as a disinfectant." In essence, $Cl_2$ will readily react with the protective carbohydrate-based glycocalyx structure which surrounds the encased micro-organisms, so that much, if not all, of its cidal capacity is vitiated by the time any $Cl_2$ can reach and destroy those organisms. $ClO_2$, on the other hand, has limited reaction with those carbohydrate superstructure components and can more substantially reach the organisms and destroy them. It does so by selective oxidation of more labile amino acids comprising the protein-containing cell walls of the organisms, thereby affecting cell-wall permeability leading to cell death.

In several relevant publications by Szabo et al., one report discussed measuring " . . . the profiles of chlorine dioxide in a biofilm as a function of depth into the biofilm." The report continued by stating that the chlorine dioxide microelectrode they used had a linear response . . . up to a $ClO_2$ concentration of 0.4 mM $ClO_2$ (27 ppm) and profiles showed depletion of disinfectant at 100 μm in the biofilm depth, indicating that $ClO_2$ may not reach bacteria in a biofilm thicker than this (100 μm depth) using a 25 mg/l (i.e., a 25 ppm) solution. These findings were consistent with those of Schlafer et al., whose model biofilms matched that of in-vivo-grown dental biofilms, where their thickness (of 7-100 μm) was similar to that of one-day-old human smooth surface plaque. Based upon this information, it would appear that there is a depletion of $ClO_2$ as the gas malodorizing solutions contain $ClO_2$ levels significantly in excess of that 25 ppm (usually 30-40 ppm.) Potentially contributing to this achievement are factors related to the poorly understood dual-species oxychlorine anion, which has been referenced in publications by specialists in fields relating to $ClO_2$ (q.v.)

As mentioned earlier in this Specification, an excess of chlorite ions in the currently marketed ProFresh® solutions has decidedly advantageous aspects. Residual chlorite, post partial conversion to $ClO_2$, allows for a continued subsequent, though incremental, production of $ClO_2$ after activation and storage of the residual chlorite solution, post-conversion. This chlorite reservoir would compensate for any $ClO_2$ evaporative losses by both periodic bottle opening by the consumer and diffusional losses through container walls. The mechanism by which the supplemental $ClO_2$ is created, however, is not by oxidation of the chlorite, from now-consumed hypochlorous acid, but by the slow disproportionation of very low levels of chlorous acid which exist in chlorite solutions at pHs at and below ca. 5-6. That reaction has been well studied, and found to have many pathways, but can be summarized by the following representative equation which occurs in more acidic chlorite solution:

$$4HClO_2 \rightarrow Cl^- + 2ClO_2 + 2H^+ + H_2O$$

At the time of teaching that technology, in Richter, U.S. Pat. No. 5,738,840, there was no apparent realization that the excess of chlorite ion also had a negative drawback, which reportedly detracted from subsequent product sales based on that patent. The disadvantageous aspects of residual unreacted chlorite ion relate negatively to the impact on consumer acceptance (i.e., the organoleptic qualities) of the marketed product, which include the following:

(a) Objectionable "saltiness;"

(b) Hypertonicity, with regard to the relative osmotic pressure of the oral rinse vis-á-vis saliva. It can be seen, from the following chemical consideration of the role of chlorite ion ($ClO_2^-$) in aqueous $ClO_2$ solutions, that selecting an optimized level of chlorite ion in such solutions will play an important role in creating the most efficient system with respect to (a) functionality; (b) osmotic compatibility with saliva vis-á-vis oral tissues; and (c) organoleptic acceptability of the appropriately optimized composition. In greater specificity, there should be:

an appropriately sufficient excess of chlorite ion to ensure continued generation and restoration of $ClO_2$, upon evaporative and diffusive losses, but not to an extent where the excess chlorite salt, e.g., sodium chlorite (a/k/a "stabilized chlorine dioxide") contributes to an unduly unpleasant, repellant "salty" perception for the product.

The Oxychlorine Complex $[Cl_2O_4]^-$

There is another major factor to be considered, however, which relates to the enhanced oxidative and germicidal activity of such mixed chlorine dioxide ($ClO_2$)-chlorite (oxychlorine) solutions which, to these inventors' awareness, has heretofore never been reported. This two-species combination in optimized molar ratio concentrations would contribute significantly to the overall success of oral rinse compositions so constructed. This discovery would seem not have been obvious to Richter, in his 840' patent, who taught therein of "oral rinse malodorant solutions comprised of significant levels of molecular chlorine dioxide at a concentration of about 3 ppm to about 200 ppm," but with no consideration regarding the contributory effect of the chlorite ion or the need for specific levels thereof to ensure the concomitant contribution of the potent oxychlorine complex without untoward negative effects of excess levels. This consideration can be further appreciated in the compositions disclosed by Richter in his 840' patent, e.g., those recited in Claim 1 thereof, which teach "an aqueous solution of molecular chlorine dioxide and a metal chlorite salt, said metal chlorite salt being present in an amount sufficient to maintain said molecular chlorine dioxide at a concentration of about 3 ppm to about 200 ppm." However, the patent is silent on any reference to the relative amount of chlorite salt to be used to generate the "about 3 ppm to about 200 ppm" of chlorine dioxide, other than specifying in dependent claim 5, " . . . wherein the metal chlorite salt is present in the solution at a concentration of about 0.01% to about 0.2%" (i.e. about 100 ppm to about 2000 ppm of such salt).

With regard to the $Cl_2O_4^-$ complex anion, it is comprised of one molecule of $ClO_2$ and one of the $ClO_2^-$ (chlorite) anion. This is a bimolecular association complex $[ClO_2.ClO_2^-]^-$ which, according to Masschelein, is an association complex that forms in near neutral aqueous solution $[ClO_2.ClO_2^-]^-$. This $[Cl_2O_4]^-$ complex is also mentioned in Kuhne, U.S. Pat. No. 4,507,285; and Kross, U.S. Pat. No. 6,284,152). "The basis for the stability of the $ClO_2$ in the presence of $ClO_2^-$ ion appears to derive from the reported existence of a bimolecular charge-transfer complex involving one molecule each of $ClO_2$ and $ClO_2^-$, as follows:

$$ClO_2 + ClO_2^- \leftrightarrow [Cl_2O_4]^- \quad Q=1.6 \text{ mol}^{-1}$$

Thus, in solutions that contain both $ClO_2$ and $ClO_2^-$, it can be expected that a portion of the $ClO_2$ will be tied up in complex form, and not be available per se as free $ClO_2$. It should be also noted that the oxidation potential of $[Cl_2O_4]^-$ is reported to be actually higher than that of $ClO_2$, so that $ClO_2$ solutions also containing $ClO_2^-$, and therefore the complex ion, would be expected to have a greater oxidation capacity than might be expected from simply that calculated from the level of $ClO_2$ present. This increased capacity would be expected to be associated with, for example, greater disinfection or a greater ability to destroy oral malodorants than a comparable $ClO_2$ solution with no additional chlorite present." (See, also Kross, U.S. Pat. No. 5,820,822) The existence of this oxidizing complex, pairing a non-ionized chlorine dioxide molecule and a chlorite ion, when together in neutral solution, was initially established in publications by Gordon et al., in 1966 and 1972. It is postulated that the basis for this complex formation arises from the fact that the chlorine dioxide molecule is an electron-deficient free radical, and can readily accept the excess electron of the chlorite ion into its molecular orbital, creating a stable dimer, with a more diffuse negative charge. Of course, it should be noted that the Richter '840 patent teaches the presence of chlorite ion in his $ClO_2$ malodorizing compositions, but, as noted above, there is no restriction on the excessive levels of chlorite that they can contain. Further, the '840 patent compositions can teach away from the presence of residual chlorite, sufficient to form the 1:1 composition of both oxychlorine species in $[Cl_2O_4]^-$.

As noted above, "the oxidation potential of $[Cl_2O_4]^-$ is reported to actually be higher than that of $ClO_2$." The presence of this species, among the oxychlorine species which comprise the active components of this invention and their methods of preparation probably contributes, to a non-quantifiable degree, to the enhanced, interrelated oxidative and cidal activities of the inventive disclosure. This applies to (a) malodor control; (b) destruction of the causative putrefying organisms; and (c) the cidal activity directed to the variety of oral pathogens associated with periodontal disease (most often encased in protective biofilms).

By way of illustration, using sodium chlorite as the most probable metal chlorite salt, the indicated range of chlorite anion corresponding to the 0.01% to 0.2% (100 ppm to 2,000 ppm) range of metal chlorite salt concentrations would be about 75 ppm to about 1,490 ppm of chlorite anion per se. Accordingly there is no consideration of any required concentrational relationship regarding the chlorite ion in the resulting $ClO_2$-containing solution following its partial oxidation to $ClO_2$, in the taught range of "about 3 ppm to about 200 ppm." As a matter of fact, if one attempted to practice the prior art, as taught by the '840 patent, the artisan of ordinary skill would immediately note the impossibility of oxidizing, for example, 100 ppm of chlorite ion to form more than 100 ppm of $ClO_2$, despite the designation of "about 200 ppm $ClO_2$" as the claimed upper end of that range.

As noted above, "the oxidation potential of $[Cl_2O_4]^-$ is reported to be actually higher than that of $ClO_2$." The presence of this species, among the oxychlorine species, which comprise the active components of the present invention and their methods of preparation probably contribute, to a non-quantifiable degree, to the enhanced, inter-related oxidative and cidal activities of the present invention disclosure. This applies to (a) malodor control; (b) destruction of the causative putrefying organisms; and (c) the cidal activity directed to the variety of oral pathogens associated with periodontal disease, which pathogens are most frequently encased in protective biofilms.

Accordingly, the prior art lacks an oxychlorine oral rise composition that adequately contributes to oral care and oral physiology, malodor control and the prevention of periodontal disease.

SUMMARY OF THE INVENTION

It is, therefore, an object of the present invention to provide an antimicrobial multiple oxychlorine-containing oral rinse composition having an oral tissue compatibility, for the prevention and treatment of oral malodor, tooth decay and periodontal disease.

It is a further object of the present invention to provide an antimicrobial multiple oxychlorine-containing oral rinse composition which includes a chlorine dioxide-containing oxychlorine oral malodor control solution, wherein such solution contains a sufficient chlorite ion reservoir to replenish evaporative and/or diffusive loss of active agent while concomitantly providing improved physiological oral tissue compatibility.

It is still a further object of the present invention to provide an antimicrobial multiple oxychlorine-containing oral rinse aqueous composition with a concomitantly enhanced palatability by balancing acceptable taste and optimizing the chlorite reservoir level needed for the extended oxychlorine activity.

An additional object of the present invention is to provide an antimicrobial multiple oxychlorine-containing oral rinse composition which, in solution, provides an enhanced palatability and an optimized chlorite reservoir, and exerting an osmotic pressure that comports with that of human saliva and oral tissues.

A still further object of the present invention is to provide an antimicrobial multiple oxychlorine-containing oral rinse composition having enhanced palatability, extended life, oral cavity compatibility and optimized chlorine dioxide-chlorite molar ratios having antimicrobial properties that further suit their use in the oral cavity.

Yet a further object of the present invention is to provide an antimicrobial multiple oxychlorine-containing oral tissue-compatible rinse composition that is effective against those bacterial species in the oral cavity which are responsible for oral malodorant production as well as the types of microorganisms harbored in oral biofilms, including dental plaque and subsequent oral disease formation e.g., gingivitis and periodontitis.

The foregoing and related objects are achieved by the presently claimed invention for an antimicrobial multiple oxychlorine-containing oral rinse composition for the prevention and treatment of oral malodor, tooth decay and periodontal disease, in addition to having oral tissue compatibility and preferably, enhanced taste, which oral rinse composition comprises molecular chlorine dioxide and chlorite ion. Preferably, the chlorite ion is significantly in the form of an oxychlorine complex anion with the oxychlorine complex being comprised of molecular chlorine dioxide and chlorite ion. It is further preferable that the chlorite ion concentration with respect to molecular chlorine dioxide is in a range of chlorite:chlorine dioxide molar ratios of from about 1.25:1 to about 10:1 and, more preferably, in a range of chlorite:chlorine dioxide molar ratios of from about 1.25:to about 7.5:1.

The antimicrobial multiple oxychlorine-containing oral rinse composition of the present invention, preferably, has an osmotic pressure that lies in the range of from about 21 mosm/L to about 77 mosm/L, and more preferably in the range of approximately 30 to approximately 58 mosm/L.

The antimicrobial multiple oxychlorine-containing oral tissue-compatible rinse composition of the present invention is effective for the prevention and treatment of tooth decay and killing microorganisms that are enclosed in dental plaque biofilms, in addition to destroying pathogenic microorganisms which are associated with periodontal disease, and that are included in the group of microorganisms which form protective biofilms on oral surfaces. Pathogenic microorganisms, which form protective biofilms, are included in the group of pathogens comprising both gram-positive and gram-negative microorganisms. The gram-positive microorganisms include *Streptococcus mutans*, which forms biofilms on dental surfaces. The gram-negative microorganisms include *Actinobacillus actinomycetemcomitans, Porphyromonas gingivalis, Prevotella intermedia, Bacteroides forsythus, Campylobacter rectus, Treponema* spp. and *Eubacterium* spp. *Porphyromonas gingivalis*, a gram-negative microorganism, is known to be associated with periodontal disease and forms protective biofilms on oral surfaces.

The antimicrobial multiple oxychlorine-containing oral rinse composition of the present invention may be prepared by the oxidation of a solution comprising a chlorite salt wherein the chlorite ion lies in a concentration range of from about 7 parts per million (ppm) to no greater than about 400 ppm; and more preferably by the oxidation of a solution comprising chlorite ion in a concentration range of from about 10 ppm to about 200 ppm. It is preferred that the multiple oxychlorine-containing oral rinse composition be prepared by sequential addition of two aqueous concentrates to a chlorite ion-containing solution, wherein such aqueous concentrates comprise an acidifying agent and a buffer-producing oxidant combination. The first sequential addition of the aqueous concentrate of acidifying agent to the chlorite ion-containing solution would result in a solution pH in the range of from about pH 4.5 to about pH 6.0. The second sequential addition of the buffer-producing oxidant composition results in a final rinse solution of the claimed chlorine dioxide containing composition of from about pH 5.0 to about 6.8.

Such an acidifying agent is a buffer-forming acid that has one or more acid functions, wherein one such function has a $pK_a$ value that lies in the range of about 3.8 to about 7.1. The buffer-forming acid is preferably lactic acid, phosphoric acid, acetic acid, tartaric acid, citric acid, succinic acid, adipic acid, malic acid and a combination thereof, with the buffer-forming acid preferably being, or a combination preferably including, citric acid. The buffer-producing oxidant combination preferably comprises an oxidizing agent and a buffer-producing multivalent alkaline salt.

The oxidizing agent is preferably selected from the group of oxidizing compounds comprising an alkali metal hypochlorite/hypochlorous acid mixture, wherein the relative amounts of hypochlorite and hypochlorous acid is dependent on the pH of the alkaline mixture, and an alkali metal persulfate. With respect to the alkali metal hypochlorite/hypochlorous acid mixture oxidizing agent, the relative amounts of hypochlorite and hypochlorous acid is dependent upon the pH of the alkaline mixture, is sodium hypochlorite/hypochlorous acid.

The physiological buffer-producing salt of a multibasic acid utilized in the method for preparing the inventive composition is preferably is selected from sodium carbonate, trisodium phosphate and a combination thereof, with the inclusion of sodium carbonate being preferred.

The present invention relates to the discovery of significant improvements that can be effected in currently available dual oxychlorine chlorine dioxide and chlorite-ion containing oral malodor treatment solutions, not only in regard to their enhanced efficacy, oral acceptability and tissue compatibility, but also with respect to their ability to destroy a variety of oral bacteria known to be associated with periodontal disease.

The foregoing improvements relate, in one aspect, to the level and functional role of the chlorite anion present in such $ClO_2$-comprised, oral malodor treatment solutions. The level of chlorite in such molecular $ClO_2$-comprising solutions is important for a number of functional reasons, including:

Solution compatibility with oral mucosae vis-á-vis salivary osmotic pressure; too high or too low a chlorite level is inconsistent with the average osmotic pressure of the product users, whose oral tissues are bathed in such saliva;

Solution palatability, where a defined molar range of $ClO_2^-$:chlorite ions is needed, for both taste and for longevity of the labile gaseous $ClO_2$ agent once the solution is oxidatively activated;
(a) too low a [$ClO_2$:chlorite] ratio thereof (i.e., an overpreponderance of chlorite ion) imparts an excessive and objectionable "salty" taste to the rinse;
(b) too high a [$ClO_2$:chlorite] ratio is associated with a decreased longevity of the stored activated solution, as well as a possibly adverse effect on the functionality of the $[Cl_2O_4]^-$ complex, known to exist in [$ClO_2$:chlorite] solutions, and which provides supplementary oxidative capacity;

The above requirements for the presence of a certain level of chlorite ion in the rinse, however, run counter to the intrinsic underlying unpleasant flavor of chlorite ion solutions. Were it not for the above two necessary inclusion factors regarding chlorite ion, the most acceptable flavor of a $ClO_2$-based oral malodorant solution would be that associated with a chlorite-free solution, just one with $ClO_2$ at a level of about 3 to about 200 ppm of $ClO_2$. The goal embodied in this inventive composition is to include sufficient chlorite ion to achieve the desired ends discussed in the above paragraphs, while minimizing the intrinsic poor palatability of chlorite-containing solutions.

There is substantial microbiological evidence that components of the inventive oral rinse compositions achieve the two following two desired ends, while concomitantly destroying the sulfurous molecules characterizing oral malodor:
1. Penetrate biofilms which are precursors to, and are actually associated with periodontal disease states, and destroy representative oral gram-negative and gram-positive microorganisms, including aerobes (e.g., streptococci, lactobacilli, staphylococci, corynebacteria) and anaerobes (e.g., *P. gingivalis* and the facultative anaerobe *Strep. mutans*); and,
2. Penetrate low-oxygen areas, such as the papillae of the tongue and oral crevices, which harbor anaerobic and facultative non-aerobic fermenting organisms, and are recognized areas where oral malodorants are putrefactively generated.

Other objects and features of the present invention will become apparent when considered in combination with the following detailed description of the invention, which provides certain preferred embodiments and examples of the present invention. It should, however, be noted that the accompanying detailed description is intended to discuss and explain only certain embodiments of the claimed invention and is not intended as a means for defining the limits and scope of the invention.

DETAILED DESCRIPTION OF THE PREFERRED EMBODIMENTS

The present invention is directed to the creation of a composition and method for preparing an oxychlorine oral rinse of enhanced taste qualities and compatibility with the oral cavity, for the destruction of malodorants that are present therein, for the destruction of putrefactive microorganisms that create such malodorant compounds and, of major importance, for destroying such microorganisms characterized as gum disease pathogens. One major consideration in this achievement derives from the deeper appreciation gained by these inventors of the role and dynamics of the chlorite ion in the oxychlorine composition from which the $ClO_2$ is generated. Another consideration relates to $ClO_2$'s ability, in that oxychlorine composition, to penetrate the protective carbohydrate biofilm that is elaborated by the enclosed organism, in sufficiently quantity to destroy the encased organism without itself being vitiated by oxidative interaction with the film's carbohydrate moieties.

The inventive composition and method significantly reduces the current ProFresh® commercial composition, based on the 840' patent, comprising an initial excessive concentration of chlorite ion to a sufficient degree that still allows for the oxidative production of $ClO_2$ and the creation of the oxychlorine $[Cl_2O_4]^-$ complex therefrom, but is more conformity and/or consistent with:
1. The greater palatability of the activated solution: The taste of chlorite salt solutions, and in particular sodium chlorite solutions, is decidedly objectionable; and.
2. The osmotic pressure of saliva that bathes oral tissue: The osmotic pressure exerted by the more-palatable range of disclosed chlorite solutions serendipitously overlaps the osmotic pressure range of human saliva. Specifically, the disclosed solutions will have pressures in the 21-77 mosm/L range for humans, and close to the reported mean osmotic pressure of human saliva of 38 millosmoles/liter (mosm/L).

The inventive technology fully satisfies the need for sufficient excess of chlorite ion to allow for subsequent replenishment of any $ClO_2$ lost during use of the activated product over its use life. Such loss occurs as a result of evaporative escape of $ClO_2$ gas from the container and/or from diffusional loss through the container walls. Such replenishment occurs through the known disproportionation of the corresponding acidic form of chlorite ion, namely, chlorous acid, which will occur to an increasing degree as the pH of the solution falls below neutrality. In inventor Kross's experience strong chlorous acid solutions alone, in the absence of oxidizing chlorine, will disproportionate (i.e., change to a mixture of more stable chlorine-containing species, while preserving the total electronic balance of the reaction products) to form, at most, a maximum of 80% chlorine dioxide; although closer to, or less than a 50% yield is more often attained. The latter obtains when the acidity of the initial chlorite solution is first reduced to no less than a pH of about 5.0, prior to activation to form the desired level of $ClO_2$. The second of these reactions pertains to this replenishment phenomenon:

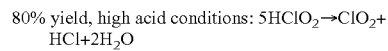

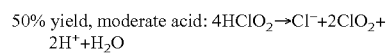

The present invention represents the unexpected convergence of a number of beneficial factors, each of which contributes significant value when devising an oral rinse that
 a)—controls oral malodor,
 b)—impacts on those microorganisms responsible for both oral malodor and periodontal diseases,
 c)—is both palatable and optimally compatible with oral tissues,
 d)—provides for extended lifetimes of the chlorine dioxide activated from residual chlorite in the composition, and
 e)—contributes the added oxidative benefit of the dimeric anion comprised of chlorine dioxide ($ClO_2$) and chlorite anion ($ClO_2^-$), specifically $Cl_2O_4^-$.

Each of these factors is considered separately below with respect to their contribution to the inventive composition, ranges of functional use, and considerations with regard to each of the other factors.

A. Palatability and Storage Stability Considerations

One significant consideration of the inventive composition relates to the degree that a balance can be struck between:

The concentration, in the activated product of the inherently objectionable, chlorine-like "salty" taste of an oral rinse containing the needed reservoir of chlorite ion ($ClO_2$)$^-$ in the oxychlorine rinse (necessarily containing dissolved $ClO_2$ gas); and, The requirement that "the needed chlorite reservoir" be of sufficient concentration to compensate for both diffusional loss of $ClO_2$ through the container walls, as well as its gaseous escape. This is likely to occur during the many times that the container is opened, closed, opened, etc. during the extended usage period of the activated malodorizing and germicidal solution.

The term "activated product" herein refers to the composition which results after the initial chlorite solution, in the "unactivated" container, is sequentially adjusted by introduction of a buffer-forming acidifying agent followed by introduction of an oxidant/buffer forming salt combination to preferentially oxidize a predetermined quantity of that chlorite to $ClO_2$ gas. The buffer-forming acidifying agent is preferably lactic acid, phosphoric acid, acetic acid, tartaric acid, citric acid, succinic acid, adipic acid, malic acid and a combination thereof. In a preferred embodiment of the present invention, the buffer-forming acidifying agent is citric acid and the oxidant is a sodium hypochlorite/hypochlorous acid aqueous composition, which rapidly converts, in the acidified medium, in whole or in part, to an enhanced hypochlorous acid composition with a diminished hypochlorite component.

The foregoing balance has been experimentally established through a series of aqueous dilutions of the currently-marketed unactivated product ensuring that the yields of $ClO_2$, upon their activation, were comparable to that in the current product. Part of the screening process was to further ensure that the "shelf-lives" of such dilutions were comparable to those of the current product. The procedure that was followed involved sequential dilution of the current, excessively high chlorite, pre-activated oral malodorant-treatment solutions, followed by appropriate acidification of the solution, followed, thereafter, by addition of appropriate levels of hypochlorous acid/hypochlorite [$HOCl/OCl^-$] solution. It would be anticipated, initially, that the volumes of [$HOCl/OCl^-$] solution would be comparable, in as much as the intended yields of $ClO_2$ would be the same. However the [$HOCl/OCl^-$] "activating" (chlorite-oxidizing) solutions are themselves alkaline. The choice was therefore made in these experiments to use the same volumes of [$HOCl/OCl^-$] in all cases, but to pre-adjust the amount of acidifier added to the more dilute solutions to compensate for the reductions in alkalinity of the diluted chlorite solutions (based on the fact that chlorite concentrates, used to prepare the unactivated oral rinse, are themselves alkaline.)

As will be explained in association with Example 1, described hereinafter, the dilutions covered the range from no addition of water to an aqueous 1:3 dilution that contained only 25% of the initial chlorite ion concentration. The "no-addition" pre-activated solution contained ca. 1,180 ppm of chlorite ion (as sodium chlorite), while the most dilute, pre-activated chlorite solution contained 295 ppm of chlorite ion. Thus, the most dilute solution had, prior to activation, ¼ of the chlorite ion as does the current pre-activated commercial product. It should be herein noted that preliminary range-finding studies had shown that aqueous dilutions greater than that of 1:3 yielded solutions that had insufficient longevity of its further reduced chlorite content for insufficient continuing replenishment of the $ClO_2$ levels that been lost by:

(a) primarily multiple twice-daily openings and removal of typical 15 ml (%-ounce) portions for use, morning and night, for the 16-oz bottle; with concomitant twice daily openings and closings, intermittent re-equilibration of the $ClO_2$ gas in the containers head space, for subsequent loss, from the diminishing volume that results from continual daily, two-week use; and, (b) secondarily gaseous diffusion through the 16-oz container which, although constructed of the virtually $ClO_2$-impermeable PETE (polyethylene terephthalate), enough of it can be diffusively lost, particularly when the solution is stored in a warm environment, the significant diminution of the $ClO_2$ gas may occur. (See, Kross, U.S. Pat. No. 6,284,152)

Upon activation of the most-diluted solution with prospective long term stability (the 1:3 composition), the residual chlorite level is reduced by about 40 ppm (to ca. 255 ppm), so that the ratio of remaining chlorite to $ClO_2$ in the solution is about 6.4:1. This is consistent with the range specified in U.S. Pat. No. 6,284,152, most preferably about 10:1 to about 1:1. In the current commercial ProFresh® rinse, upon activation, the ratio in the commercial (chlorine-tasting, "salty" solution approaches 30:1.) It should further be appreciated that lower concentrations of the activating acid solution were used in preparing the solution Groups 6 and 7 than the standard amounts used to acidify Groups 4 and 5 in Example 1, as discussed below. This was upon consideration of the lower chlorite levels (and associated alkalinity) in those groups. It should be noted that the pHs of the two 4 and 5 solutions (6.75 and 9.79), before addition of the standard levels "hypochlorite" [$HOCl/OCl^-$] oxidizer, were above the acceptable upper threshold for effective reaction which experience has shown to be pH 6.4. The objective is to prepare an aqueous solution of $ClO_2$ which contains an amount of chlorite such that the molar ratio of chlorite to $ClO_2$ ranges from about 20:1 to about 1:1, more preferably about 15:1 to about 1:1 and most preferably about 10:1 to about 1:1.

Above a pH of about 6.4, an ineffectively low relative level of hypochlorous acid ($pK_a$=7.53) exists in equilibrium with sodium hypochlorite so as to effect an acceptable rate of chlorite ion oxidation. The levels of $ClO_2$ in the Group 4 and 5 solutions, resp. 29 and 2.5 ppm) reflect that insufficiency. To correct that imbalance, as noted, Groups 6 and 7 were prepared using the same dilutions as in Groups 4 and 5, but with increased levels of acid, in order to reduce the pH levels to more appropriate levels (below pH 6.4) for efficient reactions to take place.

With respect to storage and use stability of the activated solutions, the data shown in Example 1 of this Specification reflect the levels of $ClO_2$ that remain in the various sealed containers (e.g., plastic, 16-oz PETE), that were unopened for periods of up to 78 days (ca. 2.6 months) after storage at ambient conditions. These data provide guidance for suggested usage of these solutions, based on either:

1. Pre-activation of these solutions, prior to their shipment to customers (in containers which minimize diffusive loss of $ClO_2$, as per Kross, U.S. Pat. No. 6,284,152); and,
2. Activation of these solutions by the customer, upon receipt, using solution concentrates provided by the manufacturer (the concentrations of these concentrates being dependent on the required levels of acidifying and oxidizing agents with respect to the initial chlorite concentrations of the unactivated solutions.

It should be noted, for reference herein, that the average use volume of an oral rinse solution approximates ½-ounce (ca. 15 ml), and malodorizing solutions, in particular, are recommended for use twice per day (upon arising and retiring.) Thus, a twice-per-day user of an oral rinse solution would consume ca. 1 ounce of fluid daily. The same consumption is anticipated for these solutions, even when considering their expanded use in the treatment of periodontal disease conditions. Experience has indicated that consumers prefer containers of 16-ounce capacity (ca. 473 ml) in the U.S., or a comparable 500 ml capacity in metric-use countries, based on ease of handling and duration of use of the contents. The current and conveniently-sized 16-ounce container (or 500-ml in metric-based countries) is compatible with the approximate two-week (~16 day) use of the contents of one such container. Thus, shipment of even pre-activated containers, containing reduced chlorite ion concentrations, would be compatible with the commercial distribution and delayed use of the inventive solutions.

B. Tissue Compatability Considerations

This is an area that seems to have evaded the consideration of those who have developed many commercial oral rinse products that are intended to contact oral mucosa. To these inventors' awareness, there is no oral rinse formulation, be it an OTC or $R_x$ product, where the composition of the rinse has been devised to ensure that the osmotic pressure of the formulation is comparable to that of human saliva, which bathes the oral tissues, be they the gums, the tongue, and the inner-cheek surfaces which present to the oral cavity. The only prior art that has appeared were the two patents by Speronello, et al., U.S. Pat. Nos. 8,303,939 and 8,377,423, directed to "non-cytotoxic" tooth whitening compositions and methods, where the "cytotoxicity" of chlorine dioxide-containing compositions results predominantly from the presence of oxychlorine anions. One of the considerations in developing the inventive composition and methods was to provide a solution that is most compatible with oral mucosa, consistent with other fluids intended for contact with human tissue. For example, it is well known that ophthalmic solutions are prepared with osmotic pressures comparable to those of ocular surfaces, based on, i.e., so-called "isotonic saline" (generally accorded to be about 0.9% aqueous sodium chloride.) The same consideration applies herein, where the fluid, i.e., the oral rinse, is prepared to possess an osmotic pressure that is compatible with oral tissue. That fluid is saliva, the principal protector of oral tissues produced by the salivary glands.

Disruption of the protection afforded by normal saliva, if sufficiently significant, can lead to serious complications, such as inflammation, infection, ulceration and pain of the oral tissues. Thus, the optimization goal of this inventive composition and method includes the compatibility of such compositions with the normal salivary environment of potential users of this optimized oral rinses taught herein. Specifically, the osmotic pressure of the compositions should approximate that of normal human saliva. The osmotic pressure is directly related to the soluble components comprising saliva. Sawinski et al., reported that the mean osmotic pressure of human saliva is 38 millosmoles/liter (mosm/L), a value mid-range of the 21-77 mosm/L for the subjects in their study. With respect to ophthalmic solutions, the osmotic pressure of human blood plasma (which perfuses human tissues) is approximated by an aqueous solution of 0.9% sodium chloride. Expressed as osmolality, that value is ~165 mosm/L. And, as stated, for the optimized oral rinse, it would be desirable to devise such rinse to approximate and be optimally compatible with the osmotic pressure of Sawinski's 21-77 range, and preferably come as close as feasible to the mean value of 38 mosm/L, if possible.

The inventive composition and method, directed to the multiple goals of high malodorancy, effective germicidal activity against periodontal disease-associated pathogens and selection of stable and optimally taste acceptable compositions with respect to residual chlorite content, has fortuitously achieved that desired goal as well. Specifically, the optimum composition, with the preferred ratio of residual chlorite: formed $ClO_2$.

C. Chlorine Dioxide-Chlorite Complex Considerations

An intrinsic aspect of the inventive composition and method is the presence of a certain range of a defined amount of residual chlorite ion, following oxidation of the higher and excessive level of chlorite that was initially present in the unactivated (pre-oxidized) solution. There has been a good deal of information in the published literature that indicates that the chlorite ion per se plays more than a passive role in the oxidative action of $ClO_2$-containing solutions. In fact the two dissolved oxychlorine species (chlorite ion [$ClO_2$] and $ClO_2$ gas) can combine to form a single complex oxychlorine ion. This is the $Cl_2O_4^-$ complex anion, comprised of one molecule of $ClO_2$ and one of $ClO_2^-$. This bimolecular association complex [$ClO_2.ClO_2$]$^-$ is an association complex that forms in near-neutral aqueous solutions [$ClO_2.ClO_2^-$]$^-$. This $(Cl_2O_4)^-$ complex anion is also mentioned in Kuhne, U.S. Pat. No. 4,507,285; and Kross, U.S. Pat. No. 6,284,152. The basis for the stability of the $ClO_2$ in the presence of $ClO_2^-$ ion appears to derive from the reported existence of a bimolecular charge-transfer complex involving one molecule each of $ClO_2$ and $ClO_2^-$, as follows:

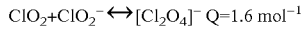
$$ClO_2 + ClO_2^- \longleftrightarrow [Cl_2O_4]^- \quad Q = 1.6 \text{ mol}^{-1}$$

Thus, in solutions that contain both $ClO_2$ and $ClO_2^-$, it can be expected that a portion of the $ClO_2$ will be tied up in complex form, and not be available, per se, as free $ClO_2$. It should be also noted that the oxidation potential of [$Cl_2O_4$]$^-$ is reportedly higher than that of $ClO_2$, so that $ClO_2$ solutions that also contain $ClO_2^-$, which solutions would therefore include levels of the complex ion, would be expected to have a greater oxidation capacity than might be expected from simply that calculated from the level of $ClO_2$ present. This increased capacity would be anticipated to provide, for example, greater disinfection as well as a greater ability to destroy oral malodorants than a comparable $ClO_2$ solution with minimal levels of chlorite present. See also Kross, U.S. Pat. No. 5,820,822. The existence of this oxidizing complex, pairing a non-ionized chlorine dioxide molecule and a chlorite ion, when together in near-neutral solutions, was initially established in publications by Gordon et al., in 1966 and 1972. The present inventors postulate that the basis for this complex formation arises from the fact that the chlorine dioxide molecule is an electron-deficient free radical and can readily accept the excess electron of the chlorite ion into its molecular orbital, creating a stable dimer, with a more diffuse negative charge. As a result, the inventive composition has a defined level of $ClO_2$, that may, in actuality, have an additional amount of that species in the form of the $[Cl_2O_4]^-$ complex.

D. Antimicrobial; Oral Disease Considerations

There are many current oral malodor products on the current market and all, to the best of these inventors' awareness, are directed to the amelioration of oral malodor. Many such products are based on so-called "stabilized chlorine dioxide," which are essentially comprised of sodium chlorite solutions and contain no measurable amounts of molecular chlorine dioxide. Others are based on the purported ability of zinc ion to destroy and/or reduce sulfurous malodorants. See, Kleinberg, U.S. Pat. Nos. 6,409,992, 6,423,300 and 6,939,790; Rolla, U.S. Pat. No. 6,344,184; Christopfel, U.S. Pat. No. 6,325,997. Only two commercial compositions claim the inclusion of free, molecular $ClO_2$; one is based on that of Roozdar, U.S. Pat. Nos. 5,651,996, 5,407,656 and 5,380,518, namely "DioxiRinse™, Chlorine Dioxide Mouthwash," and the other one "ProFresh®, based on Richter's U.S. Pat. No. 5,738,840.

Thus, of all the current compositions that are directed to the amelioration of oral malodor, there is no true molecular chlorine-dioxide based composition that is concomitantly directed to the treatment of periodontal diseases. The latter pathology is associated with, and characterized by, biofilms and their protective exopolysaccharides, within which the pathogens reside and proliferate.

The inventive compositions should preferably have chlorite solution pHs, prior to activation (i.e., addition of the oxidizing reagent to create $ClO_2$), that lie in the pH range of about 4.5 to about 6.0. The preferred reagent for this activation is an acidified sodium hypochlorite (NaClO) solution which, upon acidification, predominates in hypochlorous acid (HClO). The rationale for selecting the pH range of approximately 4.5 to approximately 6, prior to oxidation, is based on the following, which shows the relative concentration of the desired species hypochlorous acid (HOCl) needed to effect a "clean" oxidation. Below a pH of about 4, the hypochlorous acid converts to varying amounts of free chlorine ($Cl_2$), the reaction of which with chlorite ion can lead to undesired levels of chloride ($Cl^-$) and chlorate ($ClO_3^-$) ions:

| The Effect of pH on the Distribution of Chlorine Species in Water at 25° C. | | |
|---|---|---|
| pH | $Cl_2$ | HOCl |
| 2 | 52% | 48% |
| 3 | 18% | 82% |
| 4 | 0% | 100% |
| 5 | 0% | 100% |
| 6 | 0% | 100% |
| 7 | 0% | 70% |
| 7.4 | 0% | 0% |
| >7.4 | 0% | 0% |

Following the acidification of the chlorite solution to the desired 4.5 to 6 pH range, an oxidant solution, preferably comprising the predominating hypochlorite form of hypochlorous acid, is mixed into the acidified chlorite composition, where the pH and the amount of that solution is considered such that, following addition and reaction to yield the desired level of $ClO_2$, the activated oral rinse has a pH in the physiological acceptable pH range of about 5.0 to about 6.8. This upper pH value is surprising since it would appear too high to allow a significant disproportionation of any chlorous acid present, in equilibrium with chlorite ion, to provide a continuing supply of any $ClO_2$ loss. Yet experience has shown otherwise, and $ClO_2$ can indeed form, albeit at a slow rate, in a pH 6.8 solution. The lower the chlorite content, the slower the rate of generation. The rate of supplementation of $ClO_2$ from the disproportionation of chlorous acid, in near-neutral solutions, is remarkably low and significantly dependent on the minute fraction of chlorous acid in the $HClO_2 \leftrightarrow ClO_2^-$ (chlorite ion) equilibrium at solution pHs approximating neutrality, i.e., pH 7.

As an illustration, the inventors have calculated that only 1% of total chlorite exists in the chlorous acid [$HClO_2$] form at pH 3.95. And, at pH 7, only about 0.008% of total chlorite in solution exists as the minimally ionized chlorous acid. Kross has noticed, in his years of experience in oxychlorine chemistry, that concentrated chlorite solutions at pHs of 7, and even above 8, can slowly generate $ClO_2$. Even when the level of hydrogen ion available from water molecule ionization is exceedingly low ($10^{-7}$ moles/liter, at pH 7), there is a sufficient amount of $H^+$ in solution that the chlorous acid formed from available chlorite is capable of slow generation of discernible levels (detectible by odor) of $ClO_2$. (The air odor threshold of $ClO_2$ is about 0.1 part per million (ppm) in air.) And since the disproportionation reaction produces additional $H^+$ ions, the solution becomes increasingly acidic as the degradation proceeds. Thus, for the inventive compositions and methods, it is appropriate to set the final pH of the activated solution to the range of about 5.0 to about 6.8, in contrast to the prior art discussed above. This upper pH with regard to $ClO_2$ supplementation will accommodate to the lower chlorite levels herein taught, to allow the system to self-generate complementary $ClO_2$ as its dissolved levels may deplete from the enclosing container. At the upper pH of about 6.8, these inventors have calculated that about 0.002% of total chlorite exists in the chlorous acid ($HClO_2$) form. That is deemed adequate for supplementation of depleted $ClO_2$ levels based on inventor Kross's experience in oxychlorine chemistry.

Data developed in the course of the studies leading to this inventive technology are provided and discussed in the various Examples of this Specification, which data have enabled these inventors to identify desired, preferred, and most-preferred compositions for the inventive composition and methods.

Summary of pH Ranges for Acidification and Activation:
1. acidification of chlorite solution; to the 4.5 to 6 pH range; and,
2. activation of the acidified solution to achieve a final oral rinse in the approximate range of about pH 5.0 to about pH 6.8, wherein acidification is accomplished by addition to the chlorite solution of acid concentrates, comprised of organic acids (such as citric and acetic) or inorganic (such as phosphoric), which acids are capable of forming buffered solutions to create a pre-activated solution in the 4.5 to 6 pH range. Citric acid is the preferred acid for such acidification of the chlorite solution, but following activation, the buffer thus formed is then preferably supplemented by a carbonate-carbonic acid buffer. The latter is supplementarily established through inclusion of an alkaline carbonate salt in the chlorite phase. The inclusion of the latter in that phase, as will be explained, serves a dual purpose: The chlorite solution is comprised of a metal chlorite, preferably a sodium chlorite solution, the concentration of which will be elaborated upon herein below. The concentration of the chlorite in the pre-activated solution is selected such that the chlorite concentration in the activated solution lies in a range in which the rinse formed upon activation (partial oxidation of a portion of the chlorite to $ClO_2$) achieves the inventive range to comport with a)—the osmotic pressure of human saliva; b)—an improved palatability of the solution; and c)—is of adequate capacity to provide the extended generation of $ClO_2$ in the user's closed container of activated solution.

Chlorite Concentrations in the Inventive Composition

The desired range of chlorite in the pre-activated solution, most aptly expressed as the usual commercial form of sodium chlorite, should lie in the concentration range of about 0.0250% to about 0.0550%, preferably from about 0.0325% to about 0.0475%, and most preferably from about 0.0350% to about 0.0435% in aqueous solution. These concentration ranges are calculated to be sufficient for a portion of the chlorite ion to be stoichiometrically oxidized from chlorite ion, $ClO_2^-$, to $ClO_2$ gas, dissolved in the aqueous matrix. It is known that $ClO_2$, in a matrix containing chlorite ion will combine, to some degree, with chlorite to form the oxychlorine $[Cl_2O_4]^-$ complex. The $ClO_2$ level measured does not include any complexed $ClO_2$. Its level is determined spectrophotometrically in its aqueous medium at its peak absorption peak of about 359 nM based on its molar absorptivity of 1250 L $mol^{-1}$ $cm^{-1}$.

A preferred addition to the chlorite phase is a carbonate salt. Its presence serves dual functions:

1. To increase the alkalinity (i.e., the pH) of the chlorite phase in order to suppress the tendency for chlorite salts to undergo disproportionation of the minute amount of chlorous acid in equilibrium with dissolved chlorite ion. This phenomenon occurs even at pHs as alkaline as ~9, particularly when such solutions are subject to warm temperatures and/or ambient light. Sodium carbonate is a very alkaline material. As an illustrative example, a 0.001M (≈0.0106%) solution has a pH of 10.66. This alkalinity derives from the following reaction of bicarbonate with water, in which hydroxyl ion is liberated:

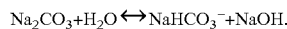
$$Na_2CO_3 + H_2O \leftrightarrow NaHCO_3^- + NaOH.$$

2. To supplement the buffering capacity of the activated solution, as already established as the preferred citrate buffer by the acid activation process. The bicarbonate buffer system is the natural basis for stabilizing blood, according to the following relationship, where the acid dissociation constant $pK_a$ of carbonic acid at 6.1 lies precisely in the physiological pH range of the activated oral rinse:

$$CO_2 + H_2O \leftrightarrow H_2CO_3 \leftrightarrow HCO_3^- + H^+$$

Chlorine Dioxide Concentration Ranges in the Oxychlorine Composition

The preferred $ClO_2$ concentration range for the claimed composition for effective malodorancy and effective periodontal disease treatment is minimally about 20 ppm to about 125 ppm; the most preferred concentration, for twice daily use directed to both oral malodor control and the amelioration of periodontal diseases, is from about 30 ppm to about 100 ppm of measured $ClO_2$, wherein $ClO_2$ is the quantifiable component of the oxychlorine composition taught herein comprising both chlorite ion and $ClO_2$ of which the oxychlorine anion complex is not quantifiable.

Oxidants and pH Considerations in Converting Chlorite Ion to Chlorine Dioxide

There are a number of reactions available for the direct conversion, mole per mole, of the chlorite ion to $ClO_2$, including the preferred hypochlorous acid system, as shown below:

$$HOCl + 2ClO_2^- \rightarrow 2ClO_2 + 2Cl^- + OH^- \tag{1}$$

Other oxidants, such as persulfate are also feasible, for example:

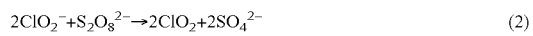
$$2ClO_2^- + S_2O_8^{2-} \rightarrow 2ClO_2 + 2SO_4^{2-} \tag{2}$$

In the preferred hypochlorite/hypochlorous acid system, it is important to avoid over-acidification, prior to activation (oxidation) of the chlorite. Specifically it is necessary to keep the acidity above ca. pH≥4, as shown in the foregoing table illustrating chlorine species present in aqueous solutions at various pHs. At a pH above ca. pH≥4, the hypochlorous acid counterpart of chlorite ion remains 100% in the HOCl form. Below that pH, wherein the $Cl_2$ species becomes increasingly contributory, various unwanted side reactions occur, and other anions, such as chloride and chlorate will form, which detract from the 1:1 stoichiometric conversion of chlorite to $ClO_2$. To avoid localized areas of greater acidity immediately upon mixing, the chlorite solution pH should be reduced rapidly to from about pH 4.5 to about pH 6.0 prior to further treatment with the oxidant. The amount of oxidant to be used is calculated a priori consistent with the chemistry of the operative oxidation system, as in Equation (1) or (2) above, after having determined the desired concentration of $ClO_2$ in the oxychlorine oral rinse composition (as described in the previous paragraph). In the preferred hypochlorous acid activation, the hypochlorous acid will be fully consumed in the oxidation process. And, as specified above, the activated oral rinse should have a final pH in the physiologically compatible pH range of from about 5.0 to about 6.8.

EXAMPLES

The following examples are presented to further illustrate and explain the present invention and should not be taken as limiting in any regard. Unless otherwise indicated, all parts and percentages are by weight:

Example 1

A study was carried out to determine the degree to which a standard, commercial unactivated oral malodorant solution could be diluted, prior to activation (i.e., acidified to an appropriate degree prior to introduction of hypochlorite), to oxidize the chlorite ion to chlorine dioxide [$ClO_2$]) to minimize the "salty" taste of the activated product. The initial concentration of chlorite ion [$ClO_2^-$] in the commercial solution prior to activation is in the range of about 1200 ppm (0.12%.) Upon activation (oxidative conversion of chlorite to the malodorizing $ClO_2$), the concentration of the latter is about 40 ppm, with over about 96% of the original sodium chlorite unreacted. Earlier experience has shown that it is important in $ClO_2$ oral malodorant solutions to include residual levels of chlorite ion to allow for the slow oxidation of the residual chlorite to $ClO_2$, to replenish small amounts which may be lost during periodic opening of the mouth rinse and/or by diffusion through the container in which the solution is stored.

The following table contains data that were obtained from the serial dilution of a standard commercial unactivated ProFresh solution, covering the range of "no addition of water" to a solution containing 25% of the initial chlorite ion concentration.' Upon activation, the remaining chlorite level is reduced by about 40 ppm, so that the ratio of remaining chlorite to $ClO_2$ in the solution is about 6.4:1.

It should be noted that the lower concentrations of the activating acid solution were used in preparing the solution used to acidify Groups 4 and 5, in anticipation of the lower chlorite levels (and associated alkalinity) in those groups. However the pHs of the two solutions (6.75 and 9.79), before addition of the standard levels hypochlorite oxidizer, were above the acceptable upper threshold for effective reaction which experience has shown to be pH 6.4. Above that pH, an ineffectively low relative level of hypochlorous acid ($pK_a$=7.53) exists in equilibrium with sodium hypochlorite so as to effect an acceptable rate of oxidation. The levels of $ClO_2$ in the Group 4 and 5 solutions, respectively, 29 and 2.5 ppm, reflect that insufficiency. To correct that imbalance, Groups 6 and 7 were prepared using the same dilutions as in Groups 4 and 5, but with increased levels of acid in order to reduce the pHs to more appropriate levels (below pH 6.4) for efficient reactions to take place.

Example 3

This study was designed to provide confirmation of the inventive compositions' intended organoleptic improvements and related properties, associated with the most dilute group, Group 7, as identified in Example 2. That composition comprised an optimal ratio of residual chlorite salt to $ClO_2$ (about 6.4:1), which was postulated to provide continued stability of the activated solution from the excess chlorite ion Data obtained from dilution studies on commercial* (PF) Oral Rinse, prior to and after activation[2]

| Gp. | Preparation Dilution→ + acid + HOCl/OCl⁻ | pH Unadjusted | Adjusted[4] | Unactivated $ClO_2^-$ ppm[3] | $ClO_2$ conc'n (ppm) after various days of storage, sealed, ambient temp. | | | |
|---|---|---|---|---|---|---|---|---|
| | | | | | T = 0 | T = 6 | T = 36 | T = 78 |
| 1 | No dilution. Activated with A&B[1] | 5.94 | — | 1180 | 39.5 | 40.5 | 44.7 | 33.0 |
| 2 | 2 PF:1 $H_2O$ | 6.25 | — | 786 | 37.5 | 35.8 | 34.7 | 28.0 |
| 3 | 1 PF:1 $H_2O$ | 6.26 | — | 590 | 36.0 | 33.8 | 31.6 | 31.0 |
| 4 | 1 PF:2 $H_2O$ | 6.75 | — | 373 | 29.0 | 28.1 | 25.6 | 22.7 |
| 5 | 1 PF:3 $H_2O$ | 9.79 | — | 295 | 0.25 | — | — | 1.32 |
| 6 | 1 PF:2 $H_2O$ | — | 6.12 | 373 | 31.0 | 37.3 | 34.2 | 30.7 |
| 7 | 1 PF:3 $H_2O$ | — | 5.88 | 295 | 26.5 | 36.7 | 33.3 | 27.9 |

*ProFresh ® (PF) Oral Rinse
[1]Standard 5 ml A (Acidifier) and B (Activator) pouches per commercial container of unactivated ProFresh ® rinse, except Groups 6 and 7.
[2]All measurement data are averages of replicate determinations, except T = 78.
[3]Corresponding to a sodium chlorite concentration of 1580 ppm (0.158%) in the unactivated ProFresh ® liquid.
[4]Increasing acidity in Groups 4 and 5 dilutions to lower the pH of the solution, prior to activation, to facilitate oxidation of chlorite ion to $ClO_2$.

Example 2

This study was carried out to determine whether the more highly diluted oral malodorant solutions (with demonstrated equivalent efficacy to the current commercial product) have the anticipated greater taste acceptability than that of the "saltier/metallic"-tasting (current) ProFresh® oral malodorant solution about which current consumers have often offered their complaints. With that goal, a subsequent set of solutions were prepared, comparable to the set in Example 1, for their organoleptic evaluation by a taste panel. Groups 4 and 5 were prepared as in Example 1, to verify the earlier conclusions, although they were not intended for taste evaluation. The relevant data obtained from this replication were, as follows, with $ClO_2$ levels measured several hours after preparation and transport to the taste panel coordinator:

| Gp. | Preparation Dilution + acid + HOCl | pH unadjusted | adjusted | chlorite $ClO_2^-$ ppm | $ClO_2$ conc'n (ppm) T = ~2 hours |
|---|---|---|---|---|---|
| 1 | No dilution. Activated with A&B | 6.25 | — | 1180 | 40 |
| 2 | 2 PF:1 $H_2O$ | 6.12 | — | 786 | 31 |
| 3 | 1 PF:1 $H_2O$ | 6.02 | — | 590 | 37 |
| 4 | 1 PF:2 $H_2O$ | 6.38 | — | 373 | 27 |
| 5 | 1 PF:3 $H_2O$ | 9.03 | — | 295 | 2 |
| 6 | 1 PF:2 $H_2O$ | — | 6.29 | 373 | 32 |
| 7 | 1 PF:3 $H_2O$ | — | 5.41 | 295 | 33 |

These solutions were also used for the microbiological study discussed in Example 4; excluding Group 4 and 5.

in solution. To put these data into proper context, it should be stressed that there is an underlying drawback of chlorite-containing solutions, which is their inherent unpalatability. This Example explores the degree of improvement in product oral acceptance, which can be achieved with a solution that has been optimized with respect to tissue-compatibility and activity of the activated solution against a backdrop of an inherently unappealing "salty" chlorite flavor of such solutions.

Specifically, the Example illustrates the comparative preference of current users of the high-chlorite, ProFresh® oral malodorant with respect to the more-dilute, more tissue-compatible inventive compositions, wherein both the original and inventive compositions had similar levels of dissolved $ClO_2$ (36±2 ppm.) A random group of 100 current users of the marketed product were provided with pre-activated, sealed 16 oz. PETE bottles of the inventive composition. This group of users were asked to use the test solution in their normal manner (i.e., twice daily) and render their opinion of the product vis-á-vis their recalled experience with the standard product. The opinions solicited, for them to summarize in a supplied form included:

i) Taste perception;
 ii) Odor of solution;
 iii) Residual taste in the mouth, if different; and,
 iv) Ability to control halitosis.

Of the 100 samples of the upgraded formulation that were sent out, 54 were returned by the recipients. Of those users who expressed a preference, the following information was provided (as per the above numerical designation):

i) Taste Perception:
   For the 52% of users that found a significant difference in taste, 61% of that group "liked the (test) sample better" than their recollection of the taste of the currently marketed, higher-chlorite product.

ii) Odor of Solution:

61% of the users reported that they could not discern an odor difference between the "test" product and their recollection of that of the currently marketed product. This would be expected in as much as the levels of $ClO_2$ gas in the "test" and the standard product were equivalent. Of the remaining 39% of respondents who indicated a perceived odor difference, 57% of each group "liked" the "test" solution's odor, and 43% preferred (their recollection) of the original product's. In as much as the levels of $ClO_2$ in both solutions were equal, those data cannot be given any great significance, although the possible contribution of a lowered chlorite content to the enhancement of the odor of solutions of comparable $ClO_2$ levels remains to be explored.

iii) Residual Taste in the Mouth, if Different:

56% of the respondents reported no significant difference in residual mouth taste. But for those who did report a difference, 67% preferred the more-dilute test product's residual taste in the mouth vs. the 33% who preferred the remembered taste of the current product (a 2:1 preference for the "test" product.) This is decidedly a significant difference; the "test" product was definitely less objectionable than the users recalled.

iv) Ability to Control Halitosis:

Not surprisingly, 77% of the 53 of 54 respondents who offered an opinion indicated that both solutions were equally effective in controlling halitosis, in as much as both solutions contained equivalent levels of dissolved $ClO_2$ gas. The remaining 23% of the 12 users who commented on this factor were split 42:58 (5 vs. 7) in their opinions regarding which solution was more effective. Considering the total number who commented, this is not considered significant.

Example 4

The following microbiological study was carried out to determine the tidal efficacy of the various dilutions prepared for Example 2. Data on the Groups 4 and 5 solutions, which were not activated under the appropriate acidity conditions, are not included. For this study the gram-negative organism, *Klebsiella pneumoniae* was selected to represent many of the oral pathogens which these inventive compositions are intended to destroy. The organism can cause the disease *Klebsiella pneumonia*, with its associated destructive changes to human lungs, inflammation and hemorrhaging. Typically these bacteria gain access after a person aspirates colonizing oropharyngeal microbes into the lower respiratory tract. Thus the selection of *Klebsiella pneumoniae* (ATCC 13883), which is an orally-related pathogen for these studies, is obvious. The details are:

Microorganisms were plated on Trypticase Soy Agar (TSA) and incubated at 35-37° C., for 18-24 hours. Organisms were then used to prepare a suspension in saline. The samples were tested by adding 0.1 ml of the microorganism suspension to 9.9 ml of the test solution in a sterile container. Samples were mixed for approximately 7 seconds and then incubated for 30 seconds. Following incubation, 1.0 ml of the mixture was added to 9 ml of D/E Neutralization Broth. A 1/10 dilution of the D/E sample in saline was prepared. Five 2.0 ml samples of the D/E broth; two 1.0 ml samples of the D/E broth and two 1.0 ml samples of the 1/10 dilution, respectively, were added to Petri plates. Approximately 10 ml of liquid Trypticase Soy Agar were added to each Petri plate and allowed to solidify. Plates were incubated at 35-37° C., for 24-48 hours, and colony forming units were counted. A control was run using 9.9 ml of saline instead of the active ingredients. The initial concentration of *K. pneumoniae* suspension in saline: $4.2 \times 10^8$ CFU/ml. The concentration of the challenge Inoculum for all the test solutions was $4.2 \times 10^6$ organisms per ml of product, which is equivalent to 6.62 logs/ml of product.

The test results are presented in the following table:

| Sample [$ClO_2$ (ppm)] | *K. pneumoniae* recovered after 30 seconds (Log#cfu/ml Product) Log reduction |
|---|---|
| Group 1 [40] | 0 (0.00) >6.62 |
| Group 2 [31] | 0 (0.00) >6.62 |
| Group 3 [37] | 0 (0.00) >6.62 |
| Group 6 [32] | 0 (0.00) >6.62 |
| Group 7 [33] | 0 (0.00) >6.62 |
| Control Recovered after 90 seconds | ≈6.17 million *K. pneumoniae* organisms in 30 sec. $3.9 \times 10^6$ (6.56) |

The conclusions to be drawn from the foregoing are that:

1. The testing of Groups 1-3, 6 and 7 found that all solutions caused a log reduction of >6.62 at 30 seconds, when tested with *K. pneumoniae*; and,
2. The control test indicated that virtually all of the organisms were recovered.

Example 5

The following microbiological biofilm kill study was run to determine the tidal efficacy of three optimized solutions of $ClO_2/ClO_2^-$ containing, on average, 35 ppm of $ClO_2$, in a chlorite solution of ca. 240 ppm of residual unactivated chlorite anion at a pH of 5.42. This involved a quantitative biofilm assay specifically developed to determine the ability of $ClO_2$ to penetrate oral biofilms. The assay involved forming a biofilm using fresh cultures of *Streptococcus mutans* and allowing them to grow in media in plastic test tubes while they were being rotated. Using the biofilm (and the organisms it contained), the assay was designed to determine the ability of the above-mentioned solutions to kill those organisms within 60 seconds.

The organism selected for this study, *Streptococcus mutans* ATCC 25175, a gram-positive and known biofilm forming organism, is the primary causative agent in the formation of dental cavities in humans. Dental plaque biofilms are responsible for many of the diseases common to the oral cavity in addition to dental caries; e.g., periodontitis, gingivitis, and the less common peri-implantitis (similar to periodontitis, but with dental implants.) It should be noted that biofilms are present on healthy teeth, as well.

Samples

Dilutions (1→4 aqueous) of "activated" commercial ProFresh oral malodor eliminating solution, each containing ca. 240 ppm of residual unactivated chlorite anion (as determined by iodometric titration):

| | | |
|---|---|---|
| Sample 1 | $ClO_2$ content = 35.0 ppm | pH 5.39 |
| Sample 2 | $ClO_2$ content = 34.7 ppm | pH 5.43 |
| Sample 3 | $ClO_2$ content = 35.0 ppm | pH 5.43 |

Materials and Methods

Microorganisms were plated on Modified Wilson Chalgren Agar (WC+) and incubated at 35-37° C., for 18-24 hours in a candle jar. Following incubation, an isolated colony of *S. mutans* was added to WC+liquid media and incubated. After 24 hours, each of approximately 20 sterile plastic tubes received a 10 µl aliquot of this growing culture and 500 µl of WC+liquid media. Two sterile tubes received 10 µl of sterile saline instead of the microorganism.

The tubes were placed on a rotator set at 1,500 RPM and incubated at 37° C. for two days. The contents of the tubes were then emptied into a suitable receptacle and the tubes were washed twice with 1.0 ml of saline, and briefly inverted and allowed to dry. A test sample of 0.750 ml was then added to each of two tubes and allowed to incubate for 60 seconds. Following this, 0.750 ml of D/E neutralizing broth was then added to each tube. The tubes were placed into an L&R Ultrasonic Quantrex sonicator bath and incubated at the top setting for 30 minutes.

Following incubation, 0.5 ml of the D/E sample was added to each of two sterile Petri plates. Approximately 10 ml of liquid WC+Agar were added to each Petri plate and allowed to solidify. Plates were incubated at 35-37° C., for 48 hours, and colonies were counted. To determine the number of microorganism in the biofilm, the above experiment was run using saline samples as positive controls. The two sterile tubes that did not receive a microorganism inoculum we also processed to serve as a negative control.

Results

| SAMPLE | Test 1 (Log#cfu/ ml Product) | Test 2 (Log#cfu/ ml Product) | Average |
|---|---|---|---|
| Control | $1.7 \times 10^2$ (2.23) | $2.2 \times 10^2$ (2.34) | $1.9 \times 10^2$ (2.28) |
| 1:3 Aqueous Dil'n Sample 1 | 0 (0.00) | 0 (0.00) | 0 (0.00) |
| Log Reduction--> | | | >(2.28) |
| Control | $1.7 \times 10^2$ (2.23) | $2.2 \times 10^2$ (2.34) | $1.9 \times 10^2$ (2.28) |
| 1:3 Aqueous Dil'n Sample 2 | 0 (0.00) | 0 (0.00) | 0 (0.00) |
| Log Reduction --> | | | >(2.28) |
| Control | $1.7 \times 10^2$ (2.23) | $2.2 \times 10^2$ (2.34) | $1.9 \times 10^2$ (2.28) |
| 1:3 Aqueous Dil'n Sample 3 | 0 (0.00) | 0 (0.00) | 0 (0.00) |
| Log Reduction--> | | | >(2.28) |
| Negative Control | 0 (0.00) | 0 (0.00) | 0 (0.00) |

Conclusions (1) Incubating *S. mutans* in plastic tubes that were being rotated resulted in microorganisms growing in a biofilm that could not be washed away with two saline washes.

(2) While variation was observed, approximately 190 CFU/ml of *S. mutans* could be removed from the biofilm by 30 minutes of sonication.

(3) Challenging the microorganisms in the biofilm with the three solutions showed a log kill of greater than 2.28 for all three solutions.

It is important to emphasize that all microorganisms were killed in all experiments and that this level of log kill reflects a limitation of the testing system, not the product being tested.

Example 6

The following microbiological biofilm kill study was run to determine the cidal efficacy of an oral rinse solution against the known oral pathogen associated with periodontal disease, *Porphyromonas gingivalis*, a biofilm-forming organism. Elevated levels of the organism have been found in periodontal lesions and low levels in healthy sites. Even with chlorhexidine gluconate, which effectively reduces the viability of biofilm-forming bacteria, such as *Porphyromonas gingivalis*, it is impossible to completely remove such biofilms. It has been inventor Kross's experience that small molecules, such as $ClO_2$, can diffuse through the glycocalyx of the biofilm, elaborated by the organism, to protect itself from cidal agents. Stronger, non-specific oxidants, such as chlorine, react with the polysaccharide structure, lose germicidal efficacy, and are incapable of destroying the enclosed organism. In this Example, a solution of the inventive composition demonstrated its ability to destroy multi-log levels of the *P. gingivalis* organism. The solution employed was one that had been optimized with respect to palatability, osmotic pressure and $ClO_2/ClO_2^-$ ratio, and contained 35 ppm of $ClO_2$, in a solution that contained ca. 240 ppm of residual unactivated chlorite anion at a pH of 5.42. A second solution was a 1→4 (ca. 9 ppm of $ClO_2$) dilution of the above, in sterile water. The study involved a quantitative biofilm assay that was specifically developed to determine the ability of $ClO_2$ to penetrate biofilms such as characteristic of *P. gingivalis*. The details are as follows:

Materials and Methods

The microorganism (*Porphyromonas gingivalis* ATCC 33277) was plated onto *Brucella* Blood Agar (BBA) and incubated at 35-37° C. for 7 days in a sealed anaerobic chamber containing an AnaeroGen™ packet. Following incubation, the organisms growing on the plate were used to prepare a suspension in Thioglycollate Broth. 500 µl of Thioglycollate Broth and 500 µl of the organism suspension were added to each of approximately ten sterile tubes. These tubes were placed into an anaerobic chamber as above and incubated at 35-37° C. for 7 days.

On the test day, eight of the tubes were selected. Each tube had a diffuse pellet on the bottom. The tubes were inverted and shaken to remove all of the fluid. The pellets were then pounded on a paper towel to further ensure that the solution had been removed. Thereafter 1.0 ml of the test solutions (non-diluted and diluted) were added to the tube and allowed to incubate for 60 seconds. The tube was again inverted and emptied. Finally 1.0 ml of Thioglycollate Broth was added to each tube to serve as both a temporary growth media and a neutralizing agent.

The tube containing the Thioglycollate Broth was either gently mixed using a Vortex Genie® mixer or was sonicated for 20 minutes in a Quantrex® sonicator. Following either mixing or sonicating, a 100 µl sample of the mixture was taken and spread over the surface of a BBA plate. To determine the number of microorganisms in the biofilm, the above experiment was run using saline or Thioglycollate Broth as positive controls. Plates were incubated in anaerobic chambers at 35-37° C. for 17 days. Upon removal the number of colonies was counted.

Results

| SAMPLE | Test 1* (Log#cfu/ ml Sample) | Test 2** (Log#cfu/ ml Sample) | Average (Log#cfu/ ml Sample) |
|---|---|---|---|
| Thioglycollate Control | $3.8 \times 10^3$ (3.58) | $1.2 \times 10^2$ (2.08) | $2.0 \times 10^3$ (3.30) |
| Saline | $1.6 \times 10^2$ (2.20) | | |
| Saline-Diluted with 3 parts sterile water | $2.7 \times 10^3$ (3.43) | | |
| Test Solution | $1.0 \times 10^1$ (1.00) | 0 (0.00) | $5.0 \times 10^0$ (0.70) |
| Test Solution Diluted with 3 parts sterile water | $1.0 \times 10^1$ (1.00) | 0 (0.00) | $5.0 \times 10^0$ (0.70) |

*This solution was mixed after incubation to remove organisms in the biofilm;
**This solution was sonicated for 20 minutes to remove organisms in the biofilm Observed Log Kill (Using Thioglycollate Values as a Control)

| SAMPLE | Thioglycollate* Control (logs) | Recovered* (logs) | Observed Kill (logs) |
|---|---|---|---|
| Solution 1 | $2.0 \times 10^3$ (3.30) | $5.0 \times 10^0$ (0.70) | 2.60 |
| Solution 1 Diluted with 3 parts sterile water | $2.0 \times 10^3$ (3.30) | $5.0 \times 10^0$ (0.70) | 2.60 |

*Average of mixed and sonicated samples.

The foregoing experimental results clearly indicate that the test solution, even when diluted with three parts of sterile water, was capable of killing at least two logs of microorganisms. Due to limitations of the procedure, this number could have actually been greater than 3.5 logs. Several variables were encountered in these experiments that were not anticipated:

1. The first of these was the effect of the pH balanced sterile saline that was used as a control in an attempt to determine the number of microorganisms in the untreated sample. It was observed that the sterile saline actually had an inhibitory effect on the ability of the organisms to be recovered, when compared to the Thioglycollate Broth. The number of colony forming units recovered by washing the tubes with saline was less than 5% of the recovery observed when using Thioglycollate Broth. This observation is further supported in that when the saline was diluted with sterile water, the number of organisms recovered increased, almost to the level observed with the Thioglycollate Broth. There are several explanations for why this may have occurred. The most obvious was that something in the saline was toxic to the very fastidious *P. gingivalis*. Saline may also have had an inhibitory effect on the ability of the microorganisms to be freed from any biofilm that had formed. Since saline clearly had an inhibitory effect, only the values obtained using the control tubes treated with Thioglycollate Broth were used to calculate the log kill.

2. The second variable was sonication. Sonication was deemed to be needed to liberate the cells from a biofilm, although sonication might have a deleterious effect on organism recovery. So samples were run in duplicate, one sample being sonicated, while the other gently mixed. Using the mixer also caused a concern that it might not have provided sufficient force to remove the microorganisms from the tube wall. The results demonstrated that the mixing force was sufficient. The mixing technique might only have released a small fraction of the organisms actually in a biofilm. As a result the observed results may have under reported the killing activity of the solution. The recovery in the Thioglycollate sample that was sonicated was less than 5% of the number recovered with mixing. The average of both methods was used in calculating the number of organisms recovered. The number of organisms in the original sample was found to be $2.0 \times 10^3$ cfu/ml. As noted, this was probably an underestimation. The number of organisms recovered after the treatment was $5.0 \times 10^0$ cfu/ml for both solutions tested. Subtracting the number of organisms recovered after treatment, from the original number of organisms used in the challenge, yielded a kill of 2.6 logs when testing with *Porphyromonas gingivalis* ATCC 33277.

The foregoing experimental results demonstrated that the "Group 7" solution as well as that same solution diluted with three parts of water were able to kill within 60 seconds of contact, *Porphyromonas gingivalis* ATCC 33277 organisms in biofilms. The kill was minimally 2.6 logs (ca. 400 organisms) and conceivably exceeded 3.5 logs (ca. 3,200 organisms.) These biofilms are directly analogous to those formed on gingival tissue and tooth surfaces in the oral cavity.

While only several embodiments of the present invention have been shown and described, it will be obvious to those skilled in the art that many modifications may be made to the present invention without departing from the spirit and scope thereof

What is claimed is:

1. A method for preparing a tissue-compatible mouth rinse solution containing an antimicrobial multiple oxychlorine oral rinse composition for the treatment of oral malodor, tooth decay and periodontal disease, comprising the steps of:
    preparing an aqueous solution comprising chlorite ion in a concentration of from about 7 ppm to about 400 ppm;
    preparing a first aqueous concentrate comprising an acidifying agent which, upon addition to said chlorite ion solution completes preparation of the first aqueous concentrate and reduces pH of said chlorite ion solution to about 4.5 to about 6.0;
    preparing a second aqueous concentrate comprising a buffer-producing oxidant combination having an oxidizing agent and a buffer compound;
    adding the first aqueous concentrate containing the acidifying agent to the chlorite ion solution; and,
    adding the second aqueous concentrate containing the buffer-producing oxidant combination to the chlorite ion solution after completing said step of adding the first aqueous concentrate to the chlorite ion solution for producing a tissue-compatible mouth rinse solution containing an antimicrobial multiple oxychlorine oral tissue-compatible rinse composition comprising chlorine dioxide and chlorite ion and having a pH of about 5.0 to about 6.8.

2. The method for preparing an antimicrobial multiple oxychlorine oral tissue-compatible rinse composition according to claim 1, wherein said antimicrobial multiple oxychlorine oral tissue-compatible rinse composition comprises molecular chlorine dioxide and chlorite ion with the chlorite ion being the predominantly present oxychlorine species.

3. The method for preparing a mouth rinse solution containing an antimicrobial multiple oxychlorine oral tissue-compatible rinse composition according to claim 2, wherein the chlorite ion to the molecular chlorine dioxide in said mouth rinse solution is in a molar ratio from about 10:1 to about 1.25:1.

4. The method for preparing a mouth rinse solution containing an antimicrobial multiple oxychlorine oral tissue-compatible rinse composition according to claim 1, wherein the chlorite ion in said chlorite ion solution is in a concentration of from about 10 ppm to about 200 ppm.

5. The method for preparing a mouth rinse solution containing an antimicrobial multiple oxychlorine tissue-compatible oral rinse composition according to claim 1 wherein said acidifying agent of said first aqueous concentrate is a buffer-forming acid having a $pK_a$ value of about 3.8 to about 7.1.

6. The method for preparing a mouth rinse solution containing an antimicrobial multiple oxychlorine oral tissue-compatible rinse composition according to claim 5, wherein said buffer-forming acid is an acid selected from the group consisting of lactic acid, phosphoric acid, acetic acid, tartaric acid, citric acid, succinic acid, adipic acid, malic acid and a combination thereof.

7. The method for preparing a mouth rinse tissue-compatible solution containing an antimicrobial multiple oxychlorine oral rinse composition according to claim 1, wherein said buffer-producing oxidant combination of said second aqueous concentrate comprises said oxidizing agent and a buffer-producing multivalent alkaline salt as said buffer compound.

8. The method for preparing a mouth rinse solution containing an antimicrobial multiple oxychlorine oral tissue-compatible rinse composition according to claim 7, wherein said oxidizing agent comprises an alkali metal hypochlorite/hypochlorous acid mixture and an alkali metal persulfate.

9. The method for preparing a mouth rinse solution containing an antimicrobial multiple oxychlorine oral tissue-compatible rinse composition according to claim 8, wherein said alkali metal hypochlorite/hypochlorous acid is sodium hypochlorite/hypochlorous acid.

10. The method for preparing a mouth rinse solution containing an antimicrobial multiple oxychlorine oral tissue-compatible rinse composition according to claim 7, wherein said buffer-producing multivalent alkaline salt is selected from the group consisting of sodium carbonate, trisodium phosphate and a combination thereof.

11. The method for preparing a mouth rinse solution containing an antimicrobial multiple oxychlorine oral tissue-compatible rinse composition according to claim 1, wherein said mouth rinse solution containing an antimicrobial multiple oxychlorine oral rinse composition has an osmotic pressure in the range of from about 21 mosm/L to about 77 mosm/L.

12. The method for preparing a mouth rinse solution containing an antimicrobial multiple oxychlorine oral tissue-compatible rinse composition according to claim 11, wherein said osmotic pressure in the range of from about 21 mosm/L to about 77 mosm/L is in the range of from about 30 mosm/L to about 58 mosm/L.

* * * * *